US007266412B2

(12) United States Patent
Stypulkowski

(10) Patent No.: US 7,266,412 B2
(45) Date of Patent: Sep. 4, 2007

(54) GENERATION OF MULTIPLE NEUROSTIMULATION THERAPY PROGRAMS

(75) Inventor: Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

(21) Appl. No.: 10/420,991

(22) Filed: Apr. 22, 2003

(65) Prior Publication Data

US 2004/0215286 A1    Oct. 28, 2004

(51) Int. Cl.
*A61N 1/00* (2006.01)
(52) U.S. Cl. .......................................... 607/48; 607/59
(58) Field of Classification Search ............... 607/30, 607/46, 48, 59, 60
See application file for complete search history.

(56) References Cited

U.S. PATENT DOCUMENTS

| | | | |
|---|---|---|---|
| 5,299,569 A | | 4/1994 | Wernicke et al. |
| 5,370,672 A | * | 12/1994 | Fowler et al. ............... 607/58 |
| 5,893,883 A | * | 4/1999 | Torgerson et al. ........... 607/59 |
| 5,938,690 A | | 8/1999 | Law et al. |
| 6,052,624 A | * | 4/2000 | Mann ........................ 607/46 |
| 6,208,902 B1 | | 3/2001 | Boveja |
| 6,308,102 B1 | | 10/2001 | Sieracki et al. |
| 6,381,496 B1 | * | 4/2002 | Meadows et al. ............ 607/59 |
| 6,449,512 B1 | * | 9/2002 | Boveja ....................... 607/41 |
| 7,110,818 B2 | * | 9/2006 | Anderson et al. ........... 607/30 |
| 2002/0022866 A1 | * | 2/2002 | Borkan ....................... 607/59 |
| 2002/0038137 A1 | | 3/2002 | Stein |
| 2002/0169485 A1 | | 11/2002 | Pless et al. |
| 2003/0036783 A1 | * | 2/2003 | Bauhahn et al. ............ 607/59 |

OTHER PUBLICATIONS

Stypulkowski, "Fitting Strategies for Multiple-Memory Programmable Hearing Instruments," American Speech Language Hearing Association, pp. 19-28 (Jul. 1993).
Chapter 5, Programming Principles; Chapter 6, Implantation Procedures; Chapter 7, Patient Management; Chapter 8, Troubleshooting; Appendix A, Reproducibles; Appendix B, Sample Informed Consent Form; Medtronic, Inc., 86 pages (1999).
Notification of Transmittal of the International Search Report and the Written Opinion of the International Searching Authority, or the Declaration for PCT Application PCT/US2004/002114, filed Jan. 26, 2004.
Notification of Transmittal of the International Preliminary Report on Patentability dated Jun. 13, 2005 for PCT Application PCT/US2004/002114, filed Jan. 26, 2004.

* cited by examiner

*Primary Examiner*—Carl Layno
*Assistant Examiner*—Eric D. Bertram
(74) *Attorney, Agent, or Firm*—Shumaker & Sieffert, P.A.

(57) ABSTRACT

Generation of multiple neurostimulation programs for delivery of neurostimulation therapy to a patient involves generation of a base program and one or more patient condition algorithms. The base program is modified according to specific algorithms associated with the patient condition algorithms to generate multiple neurostimulation programs. The patient condition algorithms specify modifications to parameters in the base program to generate programs that are better tailored to a particular condition. The base program serves as a starting point for the generation of multiple neurostimulation programs tailored to patient activities. The patient condition algorithms may correspond to different patient conditions or activities, for example, such as sitting, standing, sleeping, working, walking, running, exercising, or the like. The multiple programs can be loaded into an implanted neurostimulation device or patient programmer.

51 Claims, 10 Drawing Sheets

GENERATION OF MULTIPLE NEUROSTIMULATION THERAPY PROGRAMS

TECHNICAL FIELD

The invention relates to implanted neurostimulation devices and, more particularly, formulation of neurostimulation programs.

BACKGROUND

Neurostimulation therapy devices deliver therapy to treat a variety of symptoms or conditions, such as chronic pain, tremor, Parkinson's disease, epilepsy or psychiatric disorders. In general, an implanted neurostimulation device delivers therapy in the form of electrical stimulation pulses. An implantable neurostimulation device, for example, delivers neurostimulation therapy via leads that include electrodes located proximate to the spinal cord or within the brain of a patient.

A clinician interacts with the implanted device using an external programmer to select values for a number of programmable parameters in order to configure the neurostimulation therapy to be delivered to the patient. For example, the clinician may select an amplitude and pulse width for a stimulation waveform to be delivered to the patient, as well as a rate at which the pulses are to be delivered to the patient. The clinician also may select particular electrodes to be used to deliver the pulses, and the polarities of the selected electrodes.

The clinician ordinarily relies on patient feedback to select optimum values for the parameters. The feedback may involve extensive trial and error testing of different parameters followed by patient feedback concerning overall efficacy of the therapy. On the basis of received feedback, the clinician formulates and loads one or more programs into a patient programmer or an implanted neurostimulation device for use by the patient.

SUMMARY

In general, the invention is directed to generation of multiple neurostimulation programs for delivery of neurostimulation therapy to a patient. The neurostimulation therapy may involve, for example, treatment of pain, movement disorders, epilepsy or psychiatric disorders. The invention involves generation of a base program and one or more patient condition algorithms. The base program is modified according to the patient condition algorithms to generate multiple neurostimulation programs.

The patient condition algorithms specify rules for modification of parameters in the base program to generate programs that are better tailored to a particular condition of the patient. For example, a patient condition algorithm may specify modification of base program parameters such as pulse amplitude, pulse width, pulse rate, selected electrode combination, and duration of the delivered neurostimulation therapy. For non-pulsatile neurostimulation therapy, the patient condition algorithm may specify modification of base program parameters such as amplitude, frequency, selected electrode combination, duration, and ramp characteristics of the delivered neurostimulation therapy.

The base program serves as a starting point for the generation of multiple neurostimulation programs tailored to patient activities. The patient condition algorithms may correspond to different patient conditions such as awake, sleeping, resting, active, inactive, 'on' medication, 'off' medication, tired, depressed, anxious or the like, or patient activities, such as sitting, standing, working, walking, running, exercising, or the like. The multiple programs can be loaded into an implanted neurostimulation device or a patient programmer.

The patient selects a patient condition algorithm via a patient programmer. In response, the patient programmer transmits a pertinent program to the implanted neurostimulation device, or instructs the implanted neurostimulation device to select a stored program. Hence, the patient programmer or implanted neurostimulation device may be responsive to the selection of an condition algorithm by the patient.

Alternatively, the patient programmer or implanted neurostimulation device may be configured to automatically select different algorithms based on the time of day or detection of changes in posture, activity level, or other physiological signals sensed by the device. In either case, the implanted neurostimulation device is capable of delivering multiple neurostimulation programs based on modification of a base program according to a selected patient condition algorithm.

In one embodiment, the invention provides a method comprising generating a base program for delivery of neurostimulation therapy to a patient, and modifying the base program based on one or more patient condition algorithms to generate multiple programs for the delivery of neurostimulation therapy to the patient.

In another embodiment, the invention provides a device comprising a memory that stores one or more programs for delivery of neurostimulation therapy to a patient, and a processor that modifies a base program for delivery of neurostimulation therapy to a patient based on one or more patient condition algorithms to generate multiple programs for the delivery of neurostimulation therapy to the patient.

In an added embodiment, the invention provides a computer-readable medium comprising instructions to cause a processor to generate a base program for delivery of neurostimulation therapy to a patient, and modify the base program based on one or more patient condition algorithms to generate multiple programs for the delivery of neurostimulation therapy to the patient.

The invention may provide a number of advantages. For example, the invention permits multiple neurostimulation programs to be generated by modification of a base program. In this manner, a clinician may establish a base program and simply modify the base program to suit particular patient conditions or activities. As a result, the clinician may benefit from increased efficiency and reduced complexity, avoiding some of the extensive trial-and-error evaluation and lengthy clinical sessions usually associated with generating multiple programs.

Instead of generating multiple programs independently, a base program known to provide acceptable efficacy serves as a starting point for generation of each of the programs. Generation of multiple programs is simply a matter of applying algorithms associated with patient condition or activity to the base program to fine tune the base program parameters for application to a given patient condition, making the clinician's task easier and patient evaluation time shorter. The modifications may be limited to a therapeutic window, i.e., a range of parameters defined by a threshold for therapy efficacy and a threshold for unwanted side effects. In addition, the patient can gain access to a wider variety of therapy options.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
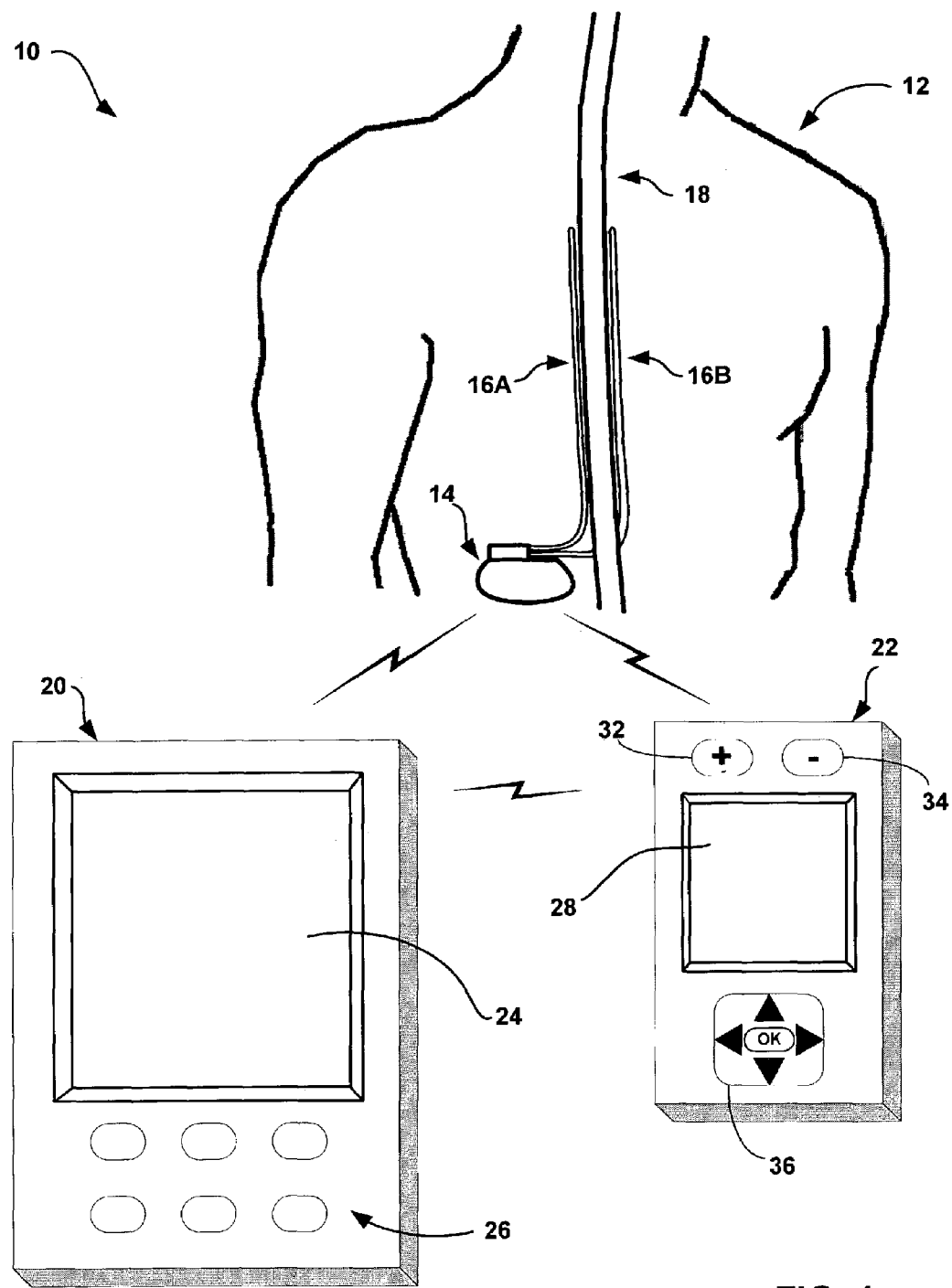
FIG. 1 is a diagram illustrating an example system for delivery of neurostimulation therapy.

FIG. 1 is a diagram illustrating an example system 10 for delivery of neurostimulation therapy to a patient 12 and context-sensitive collection of implanted neurostimulation device data. As described herein, system 10 may be configured to generate multiple neurostimulation programs by modifying a base program according to one or more patient condition algorithms. In this manner, system 10 may permit a clinician to benefit from increased efficiency, avoiding some of the extensive trial-and-error evaluation usually associated with generating multiple programs.

As shown in FIG. 1, system 10 includes an implantable medical device 14 that delivers neurostimulation therapy to patient 12. IMD 14 includes an implantable pulse generator, and delivers neurostimulation therapy to patient 12 in the form of electrical pulses. IMD 14 may be configured to deliver neurostimulation therapy for treatment of pain. Alternatively, IMD 14 may deliver neurostimulation therapy for treatment of movement disorders, epilepsy or psychiatric disorders.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12. In this case, IMD 14 may deliver deep brain stimulation (DBS) therapy to patient 12 to treat movement disorders such as tremor or Parkinson's Disease, or epilepsy or psychiatric disorders.

System 10 also includes a clinician programmer 20 and a patient programmer 22. Clinician programmer 20 may, as shown in FIG. 1, be a handheld computing device. Clinician programmer 20 includes a display 24, such as an LCD or LED display, to display information to a user, e.g., a clinician. Clinician programmer 20 may also include a keypad 26, which may be used by a user to interact with clinician programmer 20. In some embodiments, display 24 may be a touch screen display, and a user may interact with clinician programmer 20 via display 24. A user may also interact with clinician programmer 20 using peripheral pointing devices, such as a stylus or mouse. Keypad 26 may take the form of an alphanumeric keypad or a reduced set of keys associated with particular functions.

A clinician (not shown) uses clinician programmer 20 to program neurostimulation therapy for patient 12. For example, the clinician may select existing programs or specify new programs by selecting program parameter values, and test the selected or specified programs on patient 12. The clinician may receive feedback from patient 12, and store the programs and rating information associated with the programs. As will be described, clinician programmer 20 may support generation of multiple programs by modifying a base program according to algorithms associated with specific patient conditions or activities and therapeutic windows defined for the stimulation parameters, permitting the clinician to more efficiently formulate multiple programs for delivery of neurostimulation therapy for patient 12. The therapeutic window for a given stimulation parameter may define a modification range bounded by a threshold for therapy efficacy and a threshold for unwanted side effects. Hence, the algorithm may limit modifications to those that will continue to satisfy a threshold determined to delivery acceptable therapy efficacy while avoiding the threshold for unwanted side effects.

Like clinician programmer 20, patient programmer 22 may be a handheld computing device. Patient programmer 22 may also include a display 28 and input keys 32, 34, 36 to allow patient 12 to interact with patient programmer 22. In this manner, patient programmer 22 provides patient 12 with a neurostimulation therapy interface device. For example, input keys 32, 34 may be depressed by patient 12 to request an increase or decrease, respectively, in stimulation settings. Input key 36 may permit navigation within display 28. In some embodiments, display 28 may be a touch screen display, and patient 12 may interact with patient programmer 22 via display 28. In some embodiments, patient 12 may also interact with patient programmer 22 using peripheral pointing devices, such as a stylus or mouse. Patient programmer 22 may be sized for ease of portability, permitting patient 12 to carry the patient programmer during the patient's daily routine.

Patient 12 may use patient programmer 22 to control the delivery of neurostimulation therapy by IMD 14. Patient 12 may use patient programmer 22 to enter neurostimulation therapy requests. For example, patient 12 may use patient programmer 22 to start, stop or adjust neurostimulation therapy. In particular, patient programmer 22 may permit patient 12 to adjust stimulation settings such as duration, amplitude, pulse width and pulse rate, either directly or indirectly. Patient 12 may adjust stimulation settings indirectly, for example, by selecting particular programs that specify combinations of stimulation settings, as well as electrode combinations.

In accordance with an embodiment of the invention, patient 12 may use patient programmer 22 to select patient condition algorithms and thereby trigger IMD 14 to deliver different programs generated from a base program. For example, patient 12 may select patient condition algorithms that correspond to different patient conditions such as awake, sleeping, resting, active, inactive, 'on' medication, 'off' medication, tired, depressed, anxious or the like, or different patient activities, such as sitting, standing, sleeping, working, walking, running, exercising, or the like, or combinations of both conditions and activities. Such algorithms are generally referred to herein as patient condition algorithms.

In response to selection of a patient condition algorithm, programmer 22 may instruct IMD 14 to deliver pre-stored programs that correspond to the patient condition algorithms. In this case, clinician programmer 20 may generate multiple programs by modifying a base program according to patient condition algorithms, and then pre-store the multiple programs within IMD 14. Again, the patient condition algorithms may specify modifications to parameters, but limit the modifications to a therapeutic window observed to produce desirable therapeutic efficacy within substantial, undesired side effects.

Alternatively, either patient programmer 22 or IMD 14 may dynamically generate the programs from the base program in response to user input specifying selection of particular patient condition algorithms. In this case, patient programmer 22 may generate a program from a base program stored in the patient programmer, and transmit the program to IMD 14. As an alternative, programmer 22 may instruct IMD 14 to generate the program from a base program stored in the IMD. Accordingly, in various embodiments, the multiple programs may be generated within clinician programmer 20, patient programmer 22, or IMD 14 according to base programs and patient condition algorithms. In each case, the use of a base program as a starting point for formulation of multiple programs can provide added efficiency and reduced complexity.

In general, a base program may refer to data that defines parameters to control stimulation settings for neurostimulation therapy delivered by IMD 14. The multiple programs may correspond generally to the data in the base program, but incorporate modifications, additions, deletions, or other changes to the parameters and, consequently, the stimulation settings. The patient condition algorithms contain data, such as the therapeutic window for the stimulus parameters and associated rules that define the modifications, additions, deletions, or other changes to the parameters in the base program to produce the multiple programs.

Notably, the structure, format and content of the multiple programs may vary between clinician programmer 20, patient programmer 22 and IMD 14. For example, program data associated with multiple programs in clinician programmer 20 may be rearranged, compressed, converted or otherwise altered for storage in IMD 14 or patient programmer 22. Accordingly, the "program" stored in different devices, i.e., clinician programmer 20, patient programmer 22 or IMD 14, may not be identical but should contain data effective in producing similar stimulation settings when applied to IMD 14 to deliver neurostimulation therapy.

Patient programmer 22 may allow patient 12 greater control over the delivery of neurostimulation therapy within limits set by the clinician, and may lead to more effective therapy and efficient use of clinician time. Patient 12 may be able to make neurostimulation therapy requests to stop and start stimulation by IMD 14, and select or adjust stimulation settings. In addition, patient 12 may be permitted to select different programs by selecting different patient condition algorithms, as discussed above. In this manner, patient 12 may address changes in symptoms, which may occur throughout the day, or based on changes in the physical state, mental state, position, posture, or other condition or activity of the patient.

These modifications and improvements to neurostimulation therapy may occur without clinician intervention. Further, the clinician may be able to spend less time initially programming neurostimulation therapy for patient 12 by providing a variety of different programs, by modification of a base program, at implant from which patient 12 may choose. Again, the programs may specify different stimulation parameter settings based on patient condition algorithms, and allow patient 12 to tailor the neurostimulation therapy to particular situations.

The parameter modifications specified by the patient condition algorithms may include modifications to pulse amplitude (voltage or current), pulse width, pulse rate, selected electrode combinations, and duration of the delivered neurostimulation therapy. Similarly, for neurostimulation systems that employ non-pulsatile stimulation, the parameter modifications specified by the patient condition algorithms may include modifications to amplitude (voltage or current), frequency, selected electrode combinations, and duration of the delivered neurostimulation therapy.

As an, illustration, a clinician may use clinician programmer 20 to formulate and test a base program with parameter settings found to be efficacious for relief of back pain when patient 12 is in a standing position. In this case, the base program may correspond to a patient condition algorithm for standing. To generate multiple programs, the clinician applies different patient condition algorithms to the base program. Upon selection of a lying down algorithm, for example, clinician programmer 20 may modify the base program to reduce pulse amplitude or pulse width under the assumption that patient 12 experiences less pain when lying down and therefore requires less stimulation energy. This type of condition-specific modification can increase device longevity by improving consumption of battery resources with IMD 14.

As another example, upon selection of an exercise algorithm, clinician programmer 20 may modify the base program to increase pulse amplitude or pulse width, or perhaps modify the existing electrode combination. In this case, patient 12 may experience more pain when exercising, and therefore require a boost in stimulation energy or even a modification to the electrodes or polarities associated with the delivery of neurostimulation. Upon selection of multiple patient condition algorithms, clinician programmer 20 automatically generates multiple programs by modifying the base program according to parameter settings or changes specified by the pertinent patient condition algorithms. The clinician may then evaluate the efficacy of each newly created program for patient 12 via the clinician programmer 20 and IMD 14.

Hence, clinician programmer 20 may provide an efficient and convenient process for generating multiple programs. Instead of creating and experimenting with multiple programs on an independent, parallel basis, the clinician is able to start with a base program that presents acceptable efficacy and then spawn multiple programs from the base program. Again, in other embodiments, patient programmer 22 or IMD 14 itself may be configured to generate multiple programs by modifying a base program based on patient condition algorithms. However, given the relatively greater processing capability and power resources often associated with clinician programmer 20, use of the clinician programmer to generate the multiple programs and pre-store them in patient programmer 22 or IMD 14 may be desirable.

IMD 14, clinician programmer 20 and patient programmer 22 may, as shown in FIG. 1, communicate via wireless communication. Clinician programmer 20 and patient programmer 22 may, for example, communicate via wireless communication with IMD 14 using RF telemetry techniques known in the art. Clinician programmer 20 and patient programmer 22 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 22 need not communicate wirelessly, however. For example, programmers 20 and 22 may communicate via a wired connection, such as via a serial communication cable, or via exchange of removable media, such as magnetic or optical disks, or memory cards or sticks. In any event, communication mechanisms such as those described above may be used to transmit programs, as well as other data and instructions, between clinician programmer 20, patient programmer 22, and IMD 14.

Figure 2:
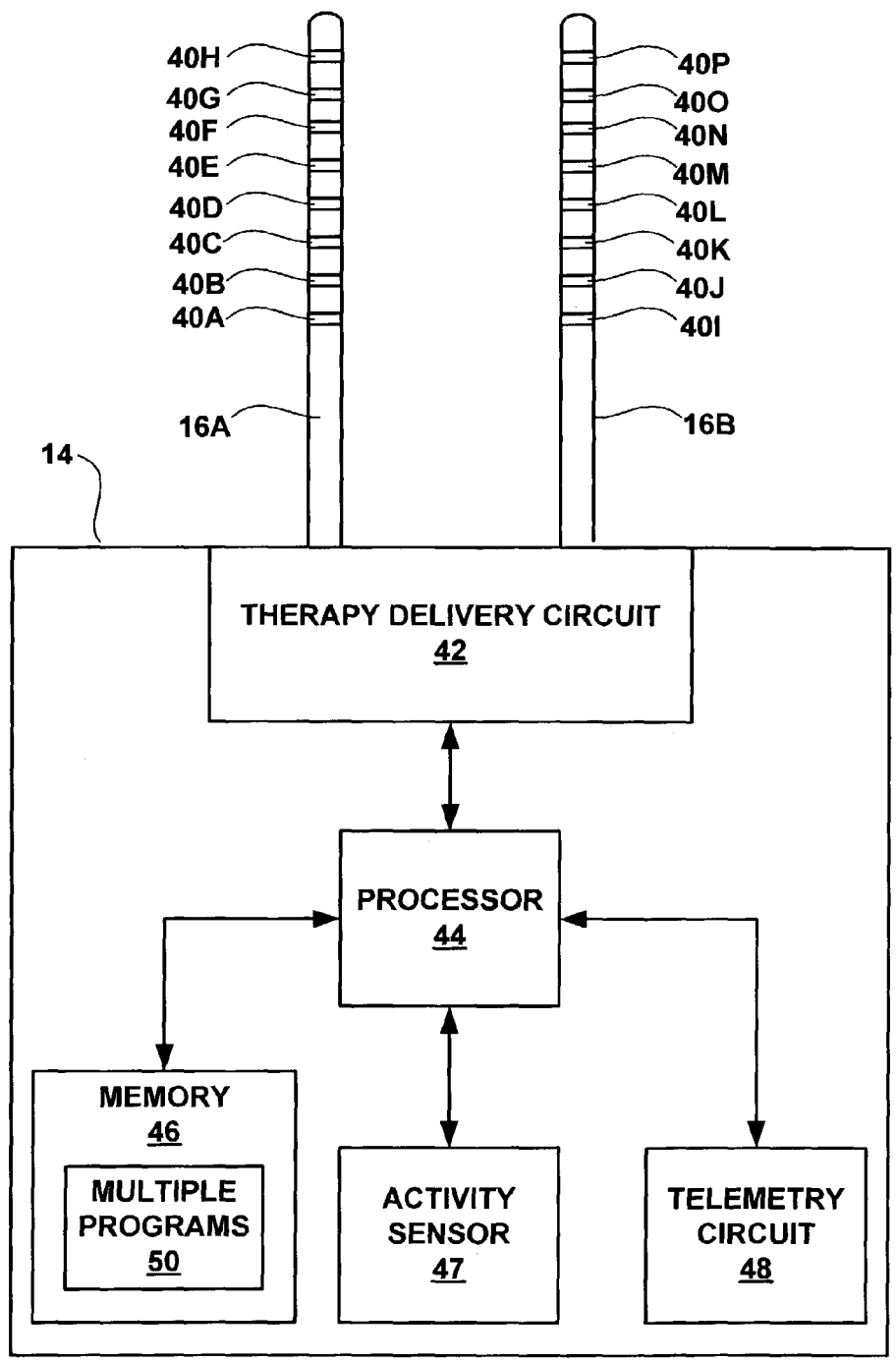
FIG. 2 is a block diagram illustrating an example implantable medical device for delivering neurostimulation therapy to a patient.

FIG. 2 is a block diagram illustrating an example configuration of IMD 14. IMD 14 may deliver neurostimulation therapy via electrodes 40A-H of lead 16A and electrodes 40I-P of lead 16B (collectively "electrodes 40"). Electrodes 40 may be ring electrodes. The configuration, type and number of electrodes 40 illustrated in FIG. 2 are merely exemplary. Electrodes 40 are electrically coupled to a therapy delivery circuit 42 via leads 16. Therapy delivery circuit 42 may, for example, include an output pulse generator coupled to a power source such as a battery. Therapy delivery circuit 42 may deliver electrical pulses to patient 12 via at least some of electrodes 40 under the control of a processor 44.

Processor 44 controls therapy delivery circuit 42 to deliver neurostimulation therapy according to a selected program or set of programs. Specifically, processor 44 controls therapy delivery circuit 42 to deliver electrical pulses with amplitudes, pulse widths, and rates specified by the programs. In addition, processor 44 also controls therapy deliver circuit 42 to deliver the pulses via selected subsets of electrodes 40 with selected polarities, as specified by the programs of the selected parameter set. Processor 44 may control therapy delivery circuit 42 to deliver each pulse according to a different program, thereby interleaving programs to simultaneously treat different symptoms or provide a combined therapeutic effect. Processor 44 may include a microprocessor, a controller, a DSP, an ASIC, an FPGA, discrete logic circuitry, or the like.

IMD 14 also includes a memory 46. In some embodiments, memory 46 may store multiple stimulation programs that are available to be selected by patient 12 for delivery of neurostimulation therapy. For example, memory 46 may store multiple programs transmitted by clinician programmer 20. As described herein, the multiple programs may be formulated based on modification of a base program according to patient condition algorithms. Accordingly, clinician programmer 20 generates the multiple programs and stores them in IMD 14. In some embodiments, however, IMD 14 may store a base program and modify the base program according to patient condition algorithms transmitted or identified by patient programmer 22 to produce multiple programs. In this manner, processor 44 of IMD 14 may dynamically generate programs according to selected patient condition algorithms.

As a further embodiment, IMD 14 may store multiple programs obtained from patient programmer 22, either dynamically or as a pre-stored set of programs. Memory 46 may also include program instructions that, when executed by processor 44, cause IMD 14 to deliver neurostimulation therapy. Memory 46 may include any volatile, non-volatile, magnetic, optical, or electrical media, such as a RAM, ROM, CD-ROM, hard disk, removable magnetic disk, memory cards or sticks, NVRAM, EEPROM, flash memory, and the like.

As described above, IMD 14 may be responsive to different patient condition algorithms communicated, for example, by patient 12 via patient programmer 22. In response to selection of a patient condition algorithm, IMD 14 selects a corresponding pre-stored program or generates a program dynamically by applying the patient condition algorithm to a stored base program. Accordingly, IMD 14 may select different programs in response to user input. In addition, IMD 14 may optionally include a condition sensor 47 that detects different patient activities, activity levels, or physiological signals such as EEG or ECG. For example, condition sensor 47 may sense changes in the position, posture, activity, heart rate, or other physiologic parameter of patient 12.

In some embodiments, activity sensor 47 may include an accelerometer or other sensor capable of detecting activity level. In response to a detected change in activity level by activity sensor 47, IMD 14 may automatically select one of the programs that corresponds to a respective patient activity. Also, in some embodiments, IMD 14 or patient programmer 22 may be configured to select and apply different programs based on the time of day, i.e., given knowledge of typical conditions or activity levels at different times throughout the patient's normal daily routine.

IMD 14 also includes a telemetry circuit 48 that allows processor 44 to communicate with clinician programmer 20 and patient programmer 22. Processor 44 may receive programs to test on patient 12 from clinician programmer 20 via telemetry circuit 48 during programming by a clinician. If IMD 14 pre-stores stimulation programs in memory 46, processor 44 may receive the programs from clinician programmer 20 via telemetry circuit 48 during programming by a clinician, and later receive neurostimulation therapy requests and patient condition algorithm selections made by patient 12 from patient programmer 22 via telemetry circuit 48. The neurostimulation therapy requests may include requests to start, stop or adjust stimulation settings. In some embodiments, patient programmer 22 may store the stimulation programs, and transmit them to IMD 14 via telemetry circuit 48.

Figure 3:
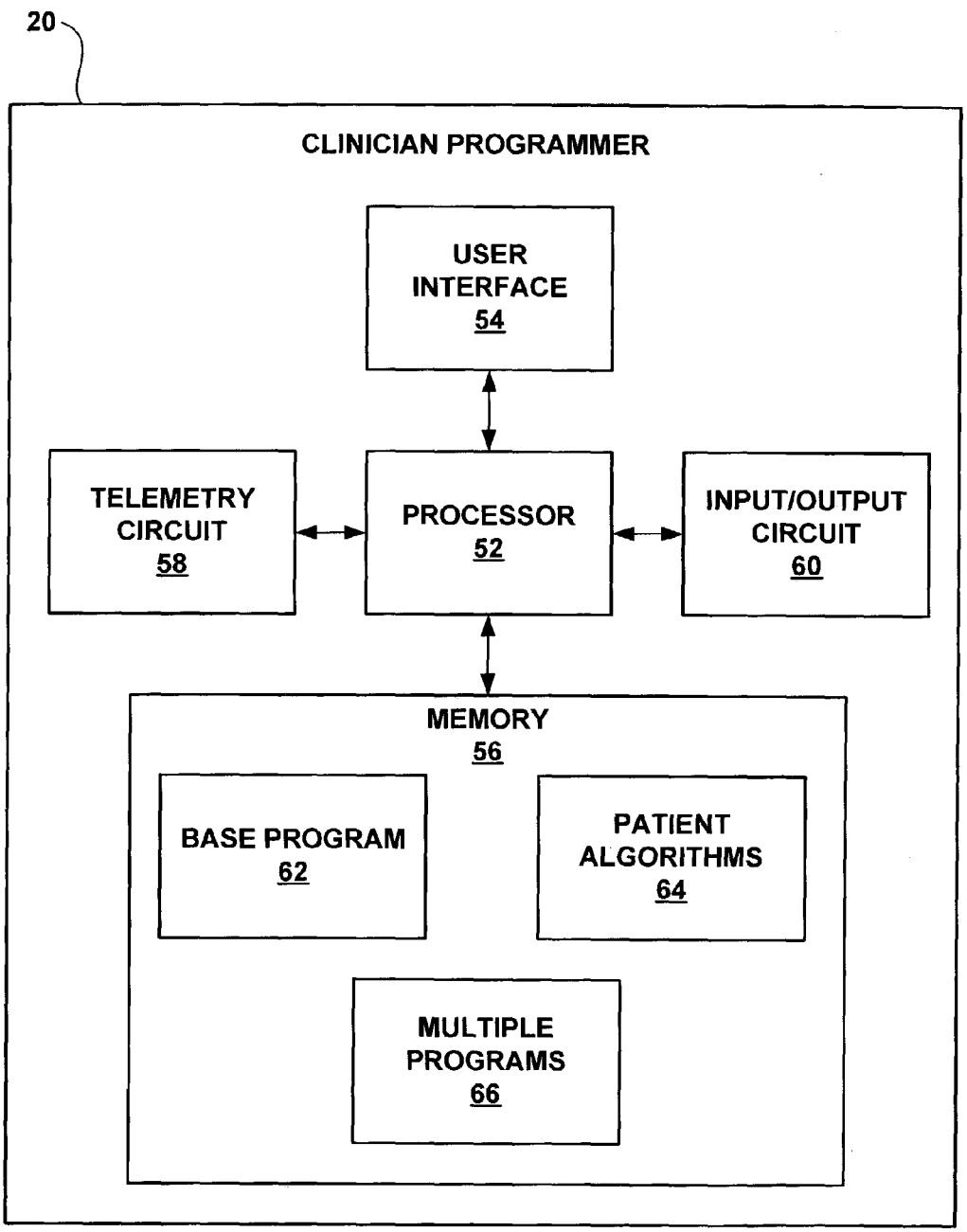
FIG. 3 is a block diagram illustrating an example clinician programmer that supports generation of multiple neurostimulation programs from a base program based on selected algorithms.

FIG. 3 is a block diagram illustrating an example configuration of clinician programmer 20. A clinician may interact with a processor 52 via a user interface 54 in order to enter neurostimulation therapy requests and thereby control delivery of neurostimulation therapy by IMD 14. User interface 54 may include display 24 and input keys 26 (FIG. 1), and may also include a touch screen or peripheral pointing devices as described above. Processor 52 may also provide a text-based interface or a graphical user interface (GUI) to facilitate interaction with the clinician. Processor 52 may include a microprocessor, a controller, a DSP, an ASIC, an FPGA, discrete logic circuitry, or the like.

Clinician programmer 20 also includes a memory 56. Memory 56 may include program instructions that, when executed by processor 52, cause clinician programmer 22 to perform the functions ascribed to clinician programmer 22 herein, including generation of a base program, and modification of the base neurostimulation program according to patient condition algorithms to generate multiple neurostimulation programs.

Memory 56 may contain a base program 62 generated by a clinician, a set of patient condition algorithms 64, and multiple programs 66 generated by modification of the base program according to the patient condition algorithms. Memory 56 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Clinician programmer 20 also includes a telemetry circuit 58 for wireless communication with IMD 14 or patient programmer 22, and optionally an input/output circuit 60 for wired communication with patient programmer 22.

Figure 4:
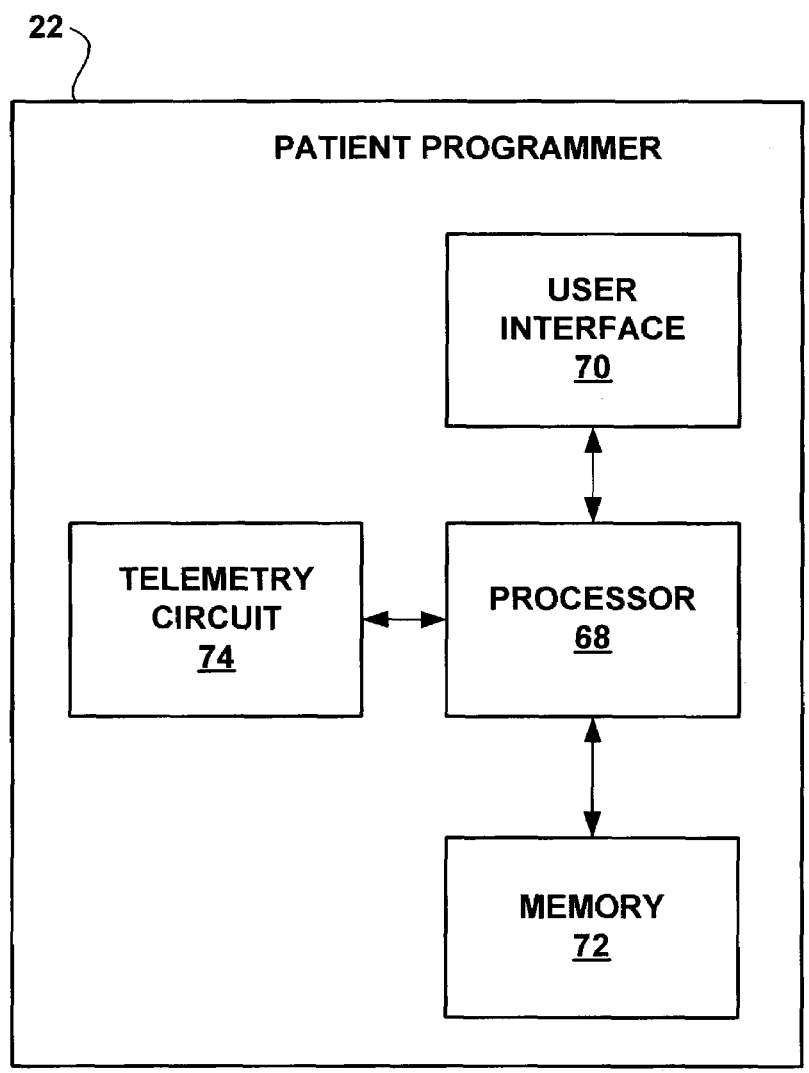
FIG. 4 is a block diagram illustrating an example patient programmer that supports generation of multiple neurostimulation programs from a base program based on selected algorithms.

FIG. 4 is a block diagram illustrating an example configuration of patient programmer 22. Patient 12 may interact with a processor 68 via a user interface 70 in order to enter neurostimulation therapy requests and select patient condition algorithms to thereby control delivery of neurostimulation therapy by IMD 14. User interface 70 may include display 28 and input keys 32, 34, 36 (FIG. 1), and may also include a touch screen or peripheral pointing devices as described above. User interface 72 may also present a text-based interface or a graphical user interface (GUI) to facilitate interaction with patient 12, as will be described in greater detail below. Processor 68 may include a microprocessor, a controller, a DSP, an ASIC, an FPGA, discrete logic circuitry, or the like.

Patient programmer 22 also includes a memory 72. Memory 72 may include program instructions that, when executed by processor 68, cause patient programmer 22 to perform the functions ascribed to patient programmer 22 herein, including processing of user input concerning selection of patient condition algorithms and user input specifying particular therapy requests, e.g., stop, start or modify therapy delivered by IMD 14. As in clinician programmer 20, memory 72 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. In addition, patient programmer 22 includes telemetry circuit 74 for communication with IMD 14, clinician programmer 20 or both.

In some embodiments, processor 68 may accept user input specifying patient condition algorithm changes, and instruct IMD 14 via telemetry circuit 74 to select pre-stored programs generated by clinician programmer 20 according to the patient condition algorithms. Alternatively, in other embodiments, processor 68 may instruct IMD 14 to dynamically generate programs corresponding to the patient condition algorithms from a base program generated by clinician programmer 20 and stored in the IMD. In still other embodiments, processor 68 of patient programmer 22 may download to IMD 14 programs generated by clinician programmer 20 and pre-stored in the patient programmer, or dynamically generate the programs from a base program generated by clinician programmer 20 and stored in the patient programmer. In each case, the additional programs are generated by modifying a base program according to patient condition algorithms.

Figure 5:
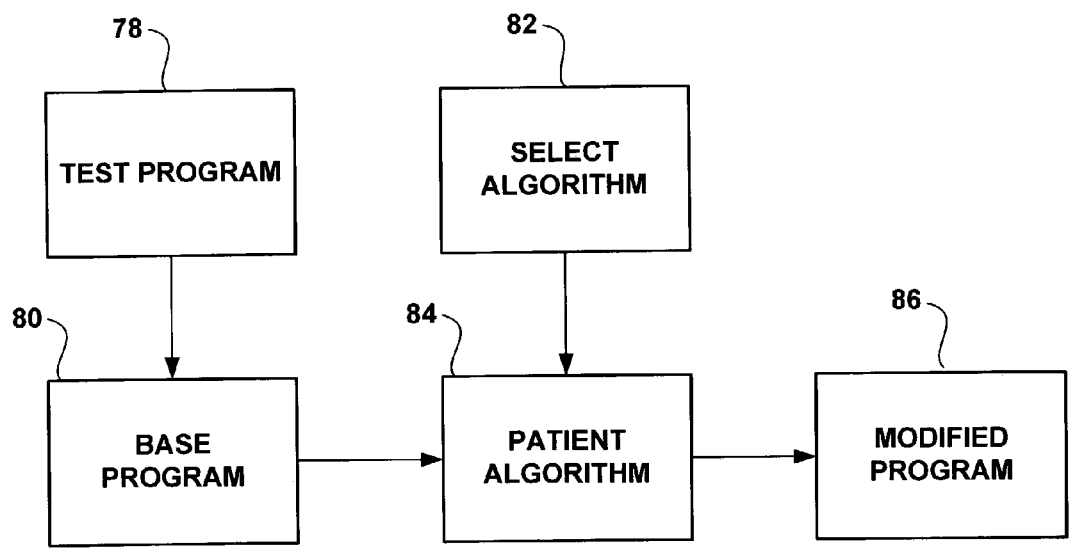
FIG. 5 is a block diagram illustrating modification of a base program to produce multiple neurostimulation programs.

FIG. 5 is a block diagram illustrating modification of a base program to generate multiple neurostimulation programs. In the example of FIG. 5, generation of multiple neurostimulation programs may be performed by a clinician in conjunction with clinician programmer 20 and IMD 14. In operation, the clinician may evaluate one or more test programs 78 by selecting particular parameter settings, such as pulse amplitude, width, rate and electrode combinations, and then applying the test programs to patient 12 via IMD 14 to evaluate efficacy. The clinician identifies a test program 78 that produces satisfactory efficacy, e.g., in terms of level of pain relief, coverage of pain relief, and side effects, and selects the identified test program as a base program 80.

To generate multiple programs for different patient activities, the clinician selects a patient condition algorithm 82. Clinician programmer 20 then applies the selected patient condition algorithm 84 to base program 80 to produce a modified program 86. Again, the patient condition algorithm may define modifications to respective base program parameter settings, within a therapeutic window specified by the algorithm or the base program. The clinician may repeat the process to produce multiple modified programs 86 corresponding to different patient condition algorithms. Alternatively, clinician programmer 20 may automatically apply multiple patient condition algorithms 84 to the base program 80 to produce the multiple modified programs 86. Upon generation of the multiple programs, clinician programmer 20 may load the programs into IMD 14 or into patient programmer 22.

The patient condition algorithms may specify modifications to stimulation parameter settings in the base program to generate programs containing different combinations of amplitude, pulse width, pulse rate, duration, electrode selection, electrode polarities and the like. The multiple programs each conform substantially to the base program, however, which serves as a starting point for the modifications specified by the patient condition algorithms. In this manner, the clinician can quickly produce multiple programs from a base program to specifically tailor neurostimulation therapy to patient conditions such as awake, sleeping, resting, active, inactive, 'on' medication, 'off' medication, tired, depressed, anxious or the like, or patient activities such as sitting, standing, sleeping, working, walking, running, exercising, or the like. The 'on' medication and 'off' medication conditions indicate whether the patient has recently taken medication. The patient condition algorithms may be identical from patient-to-patient, or customized for individual patients and may depend upon the specific disorder being treated by the neurostimulation therapy.

Figure 6:
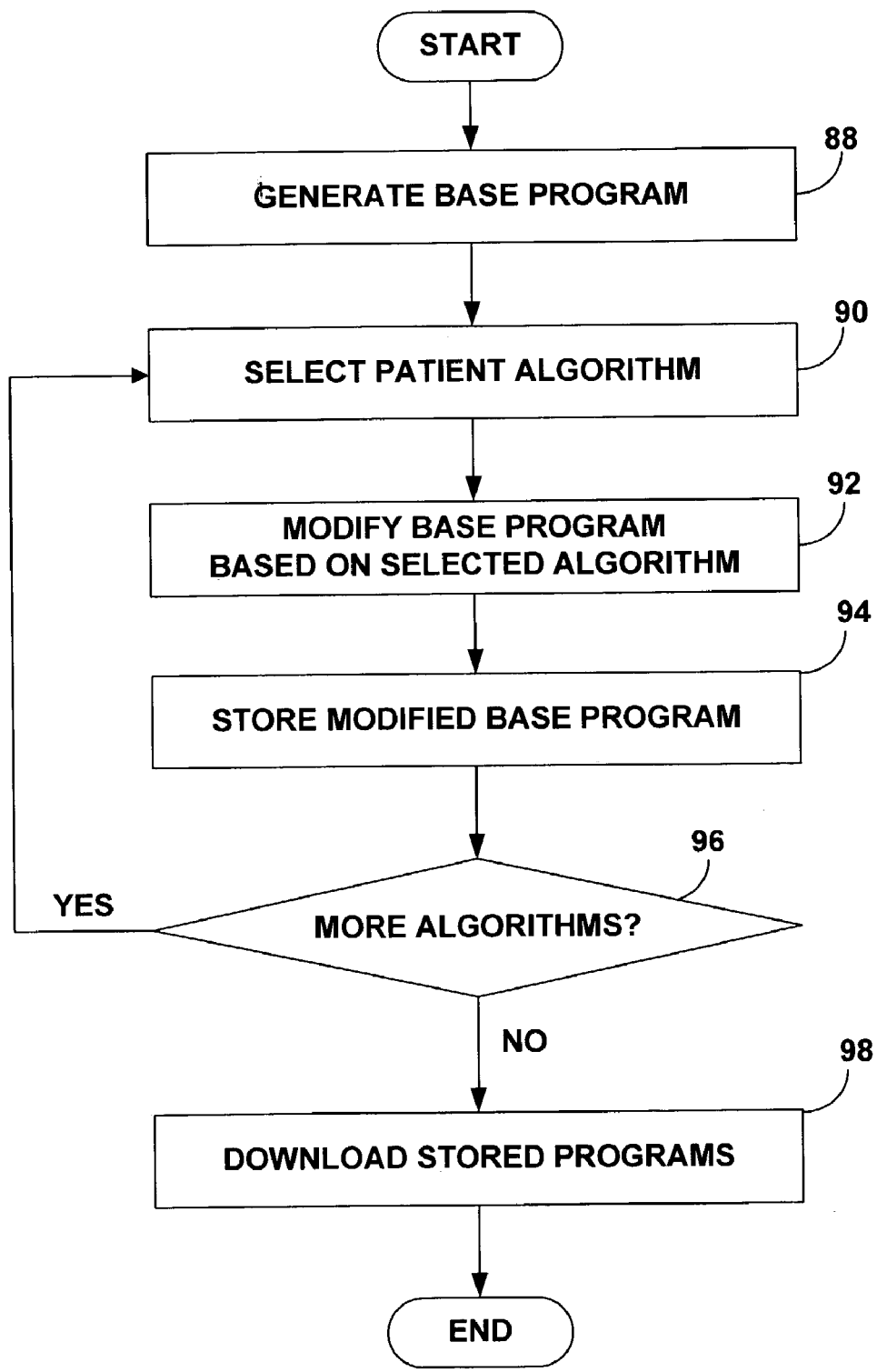
FIG. 6 is a flow diagram illustrating modification of a base program to produce multiple neurostimulation programs.

FIG. 6 is a flow diagram illustrating modification of a base program to produce multiple neurostimulation programs. As discussed above, according to different embodiments, the modifications to the base program may be performed within clinician programmer 20, patient programmer 22 or IMD 14. As shown in FIG. 6, the process starts by generating a base program (88). Again, the base program may be a program identified by the clinician as providing satisfactory efficacy for the patient. Upon selection of an algorithm (90), the process modifies the base program based on the selected algorithm (92), and stores the modified base program (94). If additional programs for other algorithms are desired (96), the process repeats. Once the desired programs are generated, they may be downloaded for storage by an appropriate device such as patient programmer 22 or IMD 14.

Figure 7:
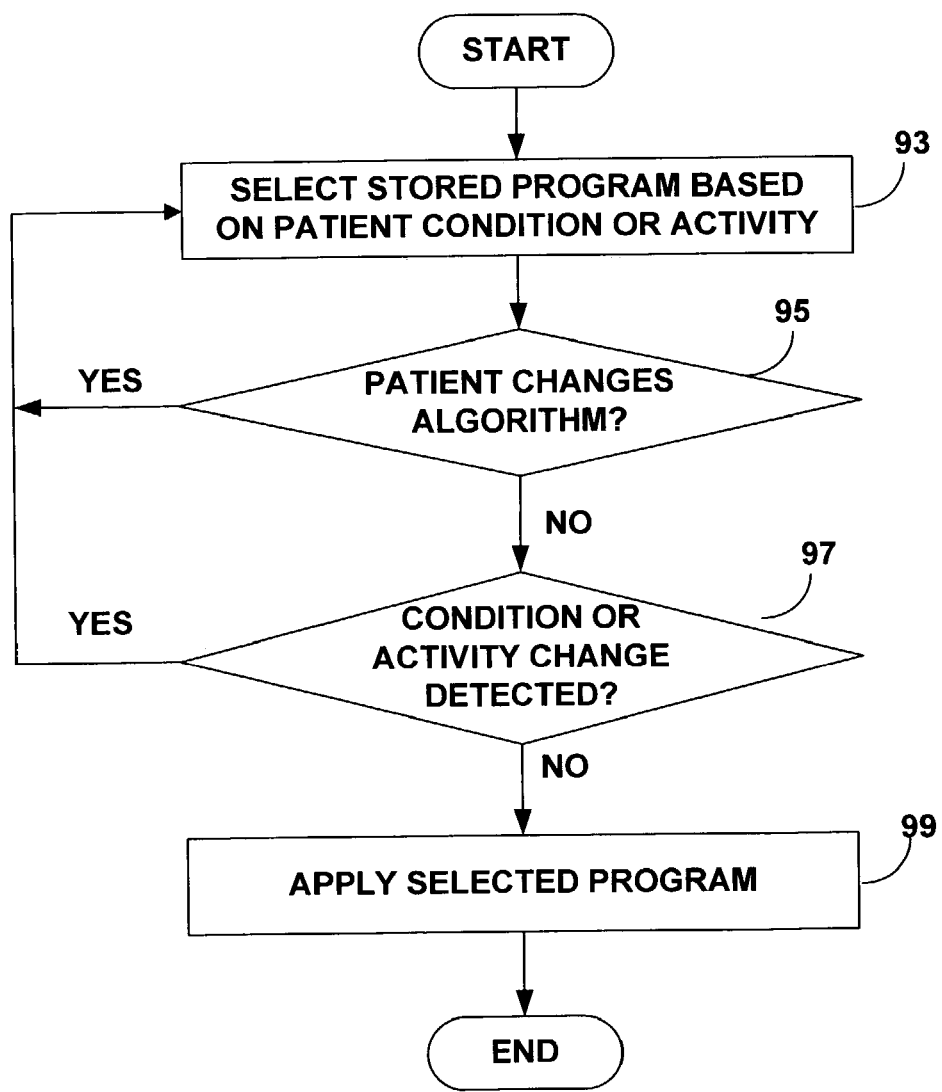
FIG. 7 is a flow diagram illustrating selection of a neurostimulation program based on selection of a patient condition algorithm.

FIG. 7 is a flow diagram illustrating selection of a neurostimulation program based on selection of a patient condition algorithm. FIG. 7 illustrates an embodiment in which IMD 14 stores multiple programs transmitted from clinician programmer 20 or patient programmer 22. As shown in FIG. 7, IMD 14 initially selects a stored program based on an indication of patient condition or activity (93). The indication of patient condition or activity may result from user input selecting a patient condition algorithm, or automated detection of patient activity level by an activity sensor 47 (FIG. 2). In addition, a patient condition such as sleep could be detected by a sensor that records and analyzes EEG information. Similarly, a patient activity such as walking could be detected by a sensor that detects acceleration.

When the patient changes the patient condition algorithm (95), IMD 14 selects a different stored program that corresponds to the condition algorithm (93). Similarly, when a condition or activity sensor 47 detects a change in patient condition or activity level (97), IMD 14 interprets a change in the patient condition algorithm and selects a corresponding stored program (93). Upon selection of the stored program, IMD 14 applies the selected program to deliver neurostimulation therapy to patient 12 (99).

Figure 8:
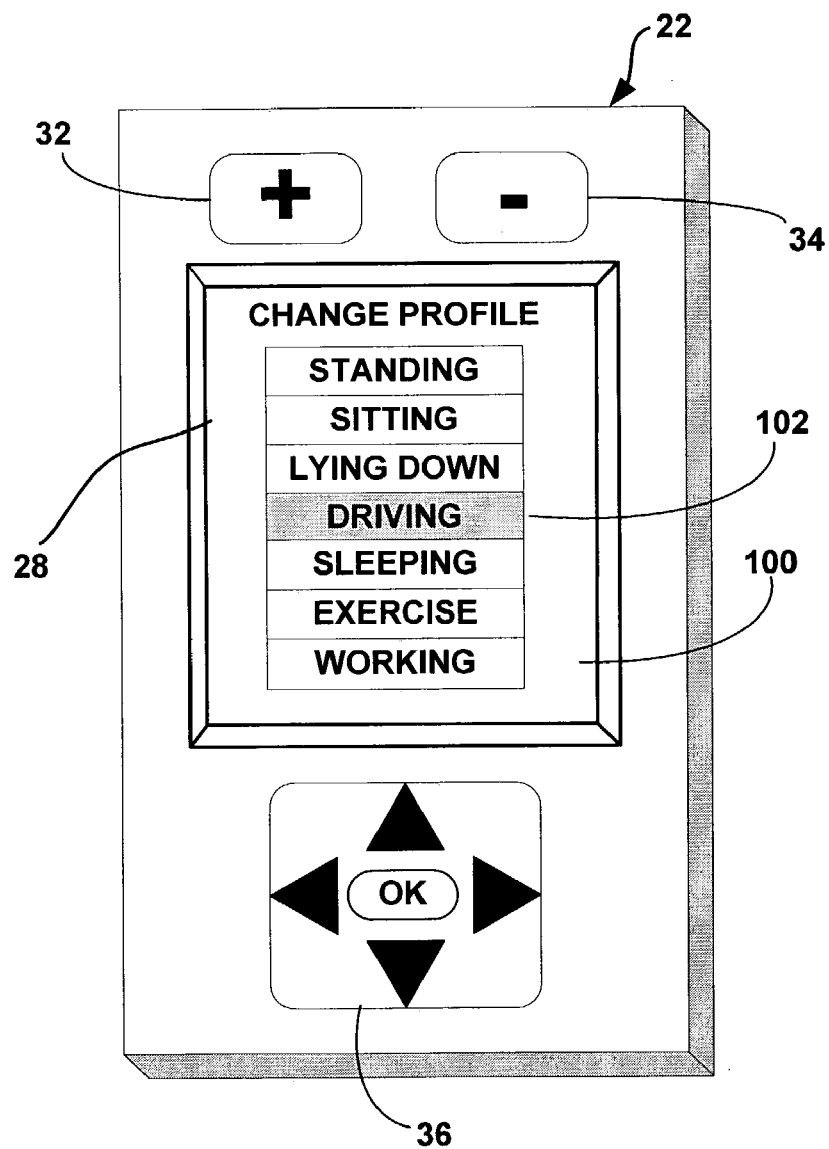
FIG. 8 is a conceptual diagram of a patient programmer presenting different patient condition algorithms for selection by a patient.

FIG. 8 is a conceptual diagram of a patient programmer 22 presenting different patient condition algorithms for selection by a patient. As shown in FIG. 8, display 28 presents a list 100 of options for selection of different patient condition algorithms. In the example of FIG. 8, list 100 designates algorithms for different patient activities. List 100 may include patient condition algorithm selections for standing, sitting, lying down, driving, sleeping, exercise, and working. The options for selection may be different depending upon the disease condition, e.g., pain, movement disorders, epilepsy, psychiatric disorders, being treated by the neurostimulation therapy.

Patient 22 selects one of the patient condition algorithms, e.g., by scrolling and clicking OK via keys 36. FIG. 8 depicts selection of the driving algorithm 102, as indicated by shading. In response, patient programmer 22 transmits an indication of the selected patient condition algorithm to IMD 14, which then selects a corresponding stored program for delivery of neurostimulation therapy. In alternative embodiments, patient programmer 22 may download stored programs to IMD 14, or dynamically generate programs from a stored base program and download the resulting program to IMD 14.

Figure 9:
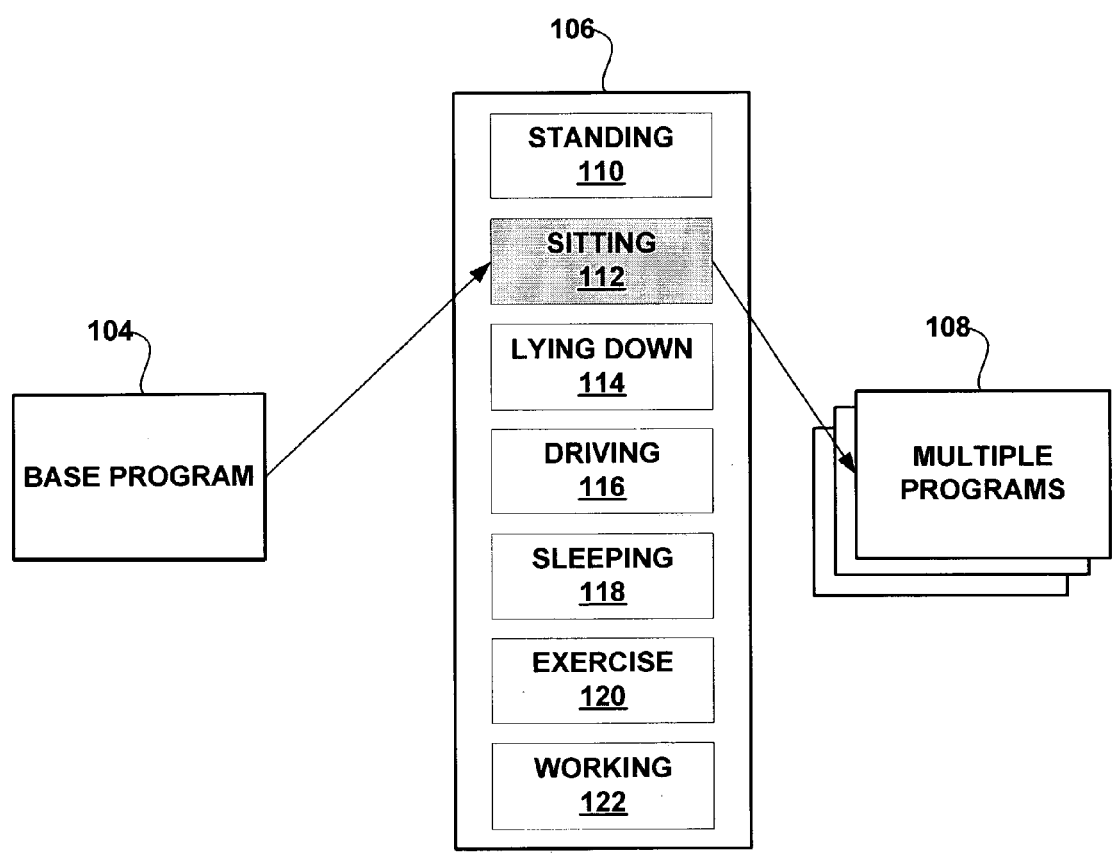
FIG. 9 is a block diagram illustrating modification of a base program based on a selected patient condition algorithm.

FIG. 9 is a block diagram illustrating modification of a base program based on a selected patient condition algorithm. As shown in FIG. 9, a base program 104 is modified according to set 106 of algorithms, including a standing algorithm 110, a sitting algorithm 112, a lying down algorithm 114, a driving algorithm 116, a sleeping algorithm 118, an exercise algorithm 120 and a working algorithm 122. Upon selection of one of the algorithms (sitting algorithm 112 in FIG. 9), the base program is modified according to parameter modifications specified by the algorithm to produce one of multiple programs 108.

Figure 10:
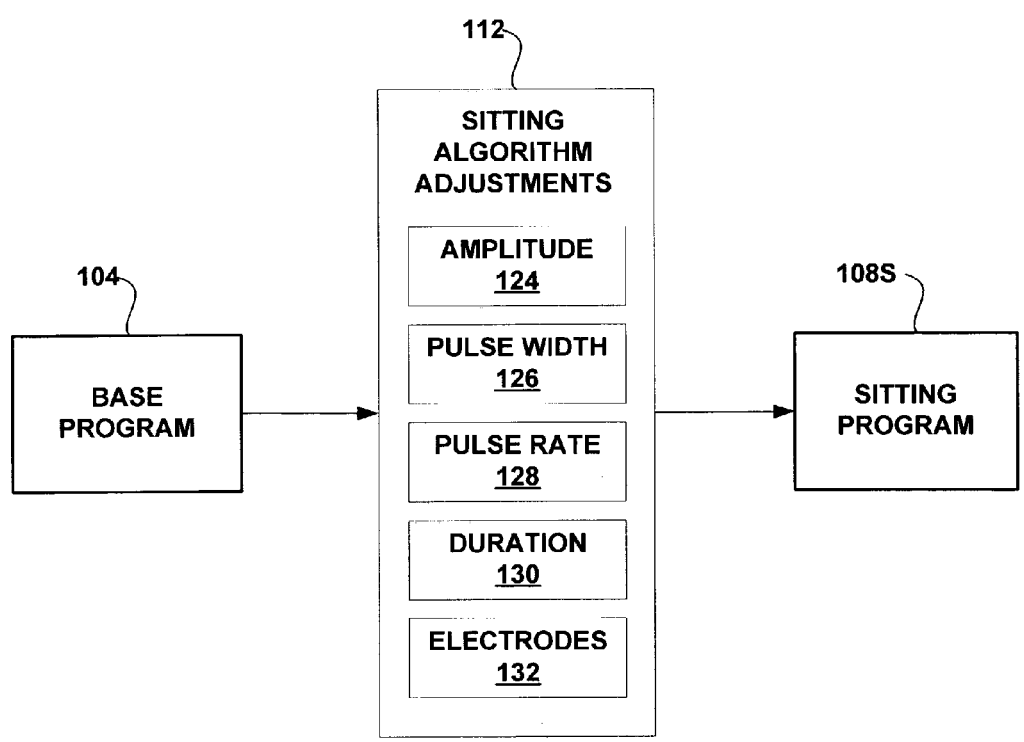
FIG. 10 is a block diagram illustrating modification of a base program based on a selected patient condition algorithm in further detail.

FIG. 10 is a block diagram illustrating modification of a base program based on a selected patient condition algorithm in further detail. As shown in FIG. 9, sitting algorithm 112 may specify adjustments to one or more of the following parameters: amplitude 124, pulse width 126, pulse rate 128, duration 130, and electrodes 132. In the event non-pulsatile neurostimulation therapy is involved, different parameter settings could be adjusted. Using sitting algorithm 112, base program 104 is modified to produce a sitting program 108S, which may be one of several programs generated based on modification of the base program.

Application of patient condition algorithms to modify a base program, as described herein, may provide advantages to the clinician and patient. For example, a clinician may establish a base program and simply modify the base program, within pre-established parameter ranges defined by a therapeutic window, to suit particular patient condition algorithms, affording increased efficiency and reduced complexity, and avoiding some of the extensive trial-and-error evaluation and lengthy clinical sessions usually associated with generating multiple programs.

Instead of generating multiple programs independently and programming individual parameters for the programs, a base program known to provide acceptable efficacy serves as a starting point for generation of each of the programs. Generation of multiple programs is simply a matter of applying patient condition algorithms to the base program to fine tune the base program parameters for application to a given patient condition, making the clinician's task easier and patient evaluation time shorter. In addition, the patient can gain access to a wider variety of therapy options.

Various embodiments of the invention have been described. However, one skilled in the art will appreciate that various modifications may be made to these embodiments without departing from the scope of the invention. These and other embodiments are within the scope of the following claims.

The invention claimed is:

1. A method comprising:
generating a base program for delivery of neurostimulation therapy to a patient;
modifying the base program based on one or more patient condition algorithms defined by data stored in a memory of a device to generate multiple programs for the delivery of neurostimulation therapy to the patient;
transmitting the base program to an implanted neurostimulation device;
receiving user input selecting one of the patient condition algorithms; and
controlling the implanted neurostimulation device to modify the base program based on the selected patient condition algorithm.

2. The method of claim 1, wherein the base program defines one or more parameters for the delivery of the neurostimulation therapy, and each of the patient condition algorithms specifies modification of at least one of the parameters.

3. The method of claim 2, wherein the parameters include neurostimulation amplitude, pulse width, frequency, therapy duration, and electrode combination and polarity.

4. The method of claim 1, wherein the patient condition algorithms include at least one of a sitting algorithm, a standing algorithm, a sleeping algorithm, a working algorithm, a walking algorithm, running algorithm, and an exercising algorithm.

5. The method of claim 1, wherein the patient condition algorithms include at least one of an awake algorithm, a sleeping algorithm, a resting algorithm, an active algorithm, so inactive algorithm, an 'on' medication algorithm, an 'off' medication algorithm, a tired algorithm, a depressed algorithm, and an anxious algorithm.

6. The method of claim 1, wherein the meurostimulation therapy includes one of spinal cord stimulation and brain stimulation.

7. The method of claim 1, wherein the base program defines parameters for the delivery of the neurostimulation therapy, and each of the patient condition algorithms specifies automatic modification of a plurality of the parameters.

8. The method of claim 1, wherein the device comprises at least one of a patient programmer device, a clinician programmer device or the implanted neurostimulation device.

9. A method comprising:
generating a base program for delivery of neurostimulation therapy to a patient:
modifying the base program based on one or more patient condition algorithms defined by data stored in a memory of a device to generate multiple programs for the delivery of neurostimuladon therapy to the patient, wherein the multiple programs are generated in a clinician orograminer device;
transmitting the multiple programs to an implanted neurostimulation device to control delivery of neurostimulation therapy to the patient by the implanted neurostimulation device; and
receiving user input selecting one of the patient condition algorithms, and controlling the implanted neurostimulation device to select one of to multiple programs that corresponds to the selected patient condition algorithm for delivery of the neurostimulation therapy to the patient.

10. The method of claim 9, wherein the device comprises at least one of a patient programmer device, the clinician programmer device or the implanted neurostimulation device.

11. A method comprising;
generating a base nrogrant for delivery of neurostimulation therapy to a patient;
transmittinautbe base program to a patient programmer device;
modifying the base program loaded into the patient programmer device based on one or more patient condition algorithms defined by data stored in a memory of a device to generate multiple programs for the delivery of neurostimulation therapy to the patient;
transmitting the modified base program to an implanted neurostimulation device; and
receiving user input selecting one of the patient condition algorithms via the patient programmer device, and modifying the base program comprises modifying the base program loaded into the patient programmer device based on the patient condition algorithms.

12. The method of claim 11, wherein the device comprises at least one of the patient programmer device, a clinician programmer device or the implanted neurostimulation device.

13. A method comprising:
generating a base program for delivery of neurostimulation therapy to a patient; and
modifying the base program based on one or more patient condition algorithms defined by data stored in a memory of a device to generate multiple programs for the delivery of neurostimulation therapy to the patient, wherein generating a base program includes:
controlling an implanted neurostimulation device to deliver neurostimulation therapy to a the patient according to a test program;
evaluating efficacy of the delivered neurostimulation therapy; and
selecting the test program as the base program if the efficacy of the delivered neurostimulation therapy is satisfactory.

14. The method of claim 13, wherein the device comprises at least one of a patient programmer device, a clinician programmer device or the implanted neurostimulation device.

15. A method comprising:
generatng a base program for delivery of neurostimulation therapy to a patient;
modifying the base program based on one or more patient condition algorithms defined by data stored in a memory of a device to generate multiple programs for the delivery of neurostimulation therapy to the patient;
detecting a type of patient condition;
selecting one of the patient condition algorithms based on the detected type of patient condition; and
controlling an implanted neurostimulation device to select one of the multiple programs that corresponds to the selected patient condition algorithm for delivery of the neurostimulation therapy to the patient.

16. The method of claim 15, wherein the device comprises at least one of a patient programmer device, a clinician programmer device or the implanted neurostimulation device.

17. A method comprising:
generating a base program for delivery of neurostimulation therapy to a patient;
modifying the base program based on one or more patient condition algorithms defined by data stored in a memory of a device to generate multiple programs for the delivery of neurostimulation therapy to the patient;
transmitting the base program to an implanted neurostimulation device;
detecting a type of patient condition;
selecting one of the patient condition algorithms based on the detected type of patient condition; and
controlling the implanted neurostimulation device to modify the base program based on the selected patient condition algorithm.

18. The method of claim 17, wherein the device comprises at least one of a patient programmer device, a clinician programmer device or the implanted neurostimulation device.

19. A method comprising:
generating a base program for delivery of neurostiniulation therapy to a patient;
modifying the base program based on one or more patient condition algorithms defined by data stored in a memory of a device to generate multiple programs for the delivery of neurostimulation therapy to the patient;
selecting one of the patient condition algorithms based on a time of day; and
controlling an implanted neurostimulation device to select one of the multiple programs that corresponds to the selected patient condition algorithm for delivery of the neurostimulation therapy to the patient.

20. The method of claim 19, wherein the device comprises at least one of a patient programmer device, a clinician programmer device or the implanted neurostimulation device.

21. A method comprising:
generating a base program for delivery of neurostimulation therapy to a patient;
modifying the base program based on one or more patient condition algorithms defined by data stored in a memory of a device to generate multiple programs for the delivery of neurostimulation therapy to the patient;
transmitting the base program to an implanted neurostimulation device;

selecting one of the patient condition algorithms based on a time of day; and controlling the implanted neurostimulation device to modify the base program based on the selected patient condition algorithm.

22. The method of claim 21, wherein the device comprises at least one of a patient programmer device, a clinician programmer device or the implanted neurostimulation device.

23. A device comprising:

a memory that stores one or more programs for delivery of neurostimulation therapy to a patient; and a processor that modifies a base program for delivery of neurostimulation therapy to the patient based on one or more patient condition algorithms defined by data stored in the memory of the device to generate multiple programs for the delivery of neurostimulation therapy to the patient, wherein the processor receives user input selecting one of the patient condition algorithms, and selects one of the multiple programs that corresponds to the selected patient condition algorithm for delivery of the neurostimulation therapy to the patient.

24. The device of claim 23, wherein the base program defines one or more parameters for the delivery of the neurostimulation therapy, and each of the patient condition algorithms specifies modification of at least one of the parameters.

25. The device of claim 24, wherein the parameters include neurostimulation amplitude, pulse width, frequency, therapy duration, and electrode combination and polarity.

26. The device of claim 23, wherein the patient condition algorithms include at least one of a sitting algorithm, a standing algorithm, a sleeping algorithm, a working algorithm, a walking algorithm, running algorithm, and an exercising algorithm.

27. The device of claim 23, wherein the patient condition algorithms include at least one of an awake algorithm, a sleeping algorithm, a resting algorithm, an active algorithm, an inactive algorithm, an 'on' medication algorithm, an 'off' medication algorithm, a tired algorithm, a depressed algorithm, and an anions algorithm.

28. The device of claim 23, further comprising a transmitter that transmits the multiple programs to an implanted neurostimulation device.

29. The device of claim 23, wherein the neurostimulation therapy includes one of spinal cord stimulation and brain stimulation.

30. The device of claim 23, wherein the base program defines parameters for the delivery of the neurostimulation therapy, and each of the patient condition algorithms specifies automatic modification of a plurality of the parameters.

31. A device comprising:

a memory that stores one or more programs for delivery of neurostimulation therapy to a patient; and a processor that modifies a base program for delivery of neurostimulation therapy to the patient based on one or more patient condition algorithms defined by data stared in the memory of the device to generate multiple programs for the delivery of neurostimulation therapy to the patient, wherein the processor receives user input selecting one of the patient condition algorithms, and modifies the base program based on the selected patient condition algorithm.

32. A device comprising:

a memory that stores one or more programs for delivery of neurostimulation therapy to a patient; and a processor that modifies a base program for delivery of neurostimulation therapy to the patient based an one or more patient condition algorithms defined by data stored in the menory of the device to generate multiple programs for the delivery at neurostimulation therapy to the patient, wherein the processor detects a type of patient condition, selects one of the patient condition algorithms based on the detected type of patient condition, and controls an implanted neurostimulation device to select one of the multiple programs that corresponds to the selected patient condition algorithm for delivery of the neurostimulation therapy to the patient.

33. A computer-readable medium comprising instructions to cause a processor to:

generate a base program for delivery of neurostimulation therapy to a patient;

modify the base program based on one or more patient condition algorithms defined by data stored in a memory of a device to generate multiple programs for the delivery of neurostimulation therapy to the patient;

receive user input selecting one of the patient condition algorithms; and control an implanted neurostimulation device to select one of the multiple programs that corresponds to the selected patient condition algorithm for delivery of the neurostimulation therapy to the patient.

34. The computer-readable medium of claim 33, wherein the base program defines one or more parameters for the delivery of the neurostimulation therapy, and each of the patient condition algorithms specifies modification of at least one of the parameters.

35. The computer-readable medium of claim 34, wherein the parameters include neurostimulation pulse amplitude, pulse width, therapy duration, and electrode combination.

36. The computer-readable medium of claim 33, wherein the patient condition algorithms include at least one of a sitting algorithm, a standing algorithm, a sleeping algorithm, a working algorithm, a walking algorithm, running algorithm, and an exercising algorithm.

37. The computer-readable medium of claim 33, wherein the patient condition algorithms include at least one of an awake algorithm, a sleeping algorithm, a resting algorithm, an active algorithm, an inactive algorithm, an 'on' medication algorithm, an 'off' medication algorithm, a tired algorithm, a depressed algorithm, and an anxious algorithm.

38. The computer-readable medium of claim 33, wherein the device is a clinician programmer device, further comprising instructions to cause the processor to generate the multiple programs in the clinician programmer device, and transmit the multiple programs to the implanted neurostimulation device to control delivery of neurostimulation therapy to a patient by the implanted neurostimulation device.

39. The computer-readable medium of claim 33, wherein the neurostimulation therapy includes one of spinal cord stimulation and brain stimulation.

40. The computer-readable medium of claim 33, wherein the base program defines parameters for the delivery of the neurostimulation therapy, and each of the patient condition algorithms specifies automatic modification of a plurality of the parameters.

41. The computer-readable medium of claim 33, wherein the device comprises at least one of a patient programmer device, a clinician programmer device or the implanted neurostimulation device.

42. A computer-readable medium comprising instructions to cause a processor to:
   generate a base program for delivery of neurostimulation therapy to a patient;
   modify the base program based on one or more patient condition algorithms defined by data stored in a memory of a device to generate multiple programs for the delivery of neurostimulation therapy to the patient;
   receive user input selecting one of the patient condition algorithms; and
   control an implanted neurostimulation device to modify the base program based on the selected patient condition algorithm.

43. The computer-readable medium of claim 42, wherein the device comprises at least one of a patient programmer device, a clinician programmer device or the implanted neurostimulation device.

44. A computer-readable medium comprising instructions to cause a processor to;
   generate a base program for delivery of neurostimulation therapy to a patient;
   modify the base program based on one or more patient condition algorithms defined by data stored in a memory of a device to generate multiple programs for the delivery of neurostimulation therapy to the patient;
   detect a type of patient condition;
   select one of the patient condition algorithms based on the detected type of patient condition; and
   control an implanted neurostimulation device to select one of the multiple programs that corresponds to the selected patient condition algorithm for delivery of the neurostimulation therapy to the patient.

45. The computer-readable medium of claim 44, wherein the device comprises at least one of a patient programmer device, a clinician programmer device or the implanted neurostimulation device.

46. A computer-readable medium comprising instructions to cause a processor to;
   generate a base program for delivery of neurostimulation therapy to a patient;
   modify the base program based on one or more patient condition algorithms defined by data stored in a memory of a device to generate multiple programs for the delivery of neurostimulation therapy to the patient;
   transmit the base program to an implanted neurostimulation device;
   detect a type of patient condition;
   select one of the patient condition algorithms based on the detected type of patient condition; and
   control the an implanted neurostimulation device to modify the base program based on the selected patient condition algorithm.

47. The computer-readable medium of claim 46, wherein the device comprises at least one of a patient programmer device, a clinician programmer device or the implanted neurostimulation device.

48. A computer-readable medium comprising instructions to cause a processor to:
   generate a base program for delivery of neurostimulation therapy to a patient;
   modify the base program based on one or more patient condition algorithms defined by data stored in a memory of a device to generate multiple programs for the delivery of neurostimulation therapy to the patient;
   select one of the patient condition algorithms based on a time of day; and
   control an implanted neurostimulation device to select one of the multiple programs that corresponds to the selected patient condition algorithm for delivery of the neurostimulation therapy to the patient.

49. The computer-readable medium of claim 48, wherein the device comprises at least one of a patient programmer device, a clinician programmer device or the implanted neurostimulation device.

50. A computer-readable medium comprising instructions to cause a processor to:
   generate a base program far delivery of neurostimulation therapy to a patient;
   modify the base program based on one or more patient condition algorithms defined by data stored in a memory of a device to generate multiple programs for the delivery of neurostimulation therapy to the patient;
   transmit the base program to an implanted neurostimulation device;
   select one of the patient condition algorithms based on a time of day; and
   control the implanted neurostimulation device to modify the base program based on the selected patient condition algorithm.

51. The computer-readable medium of claim 50, wherein the device comprises at least one of a patient programmer device, a clinician programmer device or the implanted neurostimulation device.

* * * * *

UNITED STATES PATENT AND TRADEMARK OFFICE
CERTIFICATE OF CORRECTION

PATENT NO. : 7,266,412 B2  Page 1 of 1
APPLICATION NO. : 10/420991
DATED : September 4, 2007
INVENTOR(S) : Paul H. Stypulkowski It is certified that error appears in the above-identified patent and that said Letters Patent is hereby corrected as shown below:

Col. 12, Line 58: "so inactive" should read --an inactive--

Col. 12, Line 60: "the meurostimulation" should read --the neurostimulation--

Col. 13, Line 13: "clinician orograminer" should read --clinician programmer--

Col. 13, Line 21: "of to multiple" should read --of the multiple--

Col. 13, Line 30: "base nrograntfor" should read --base program for--

Col. 13, Line 32: "transmittinautbe base" should read --transmitting the base--

Col. 13, Line 60: "to a the patient" should read --to the patient--

Col. 14, Line 44: "of neurostiniulation" should read --of neurostimulation--

Col. 15, Line 43: "an anions" should read --an anxious--

Col. 18, Line 4: "control the an" should read --control an--

Signed and Sealed this

Twenty-ninth Day of April, 2008

JON W. DUDAS
*Director of the United States Patent and Trademark Office*